(12) United States Patent
Nober et al.

(10) Patent No.: US 11,191,907 B2
(45) Date of Patent: Dec. 7, 2021

(54) CAP FOR AN INJECTION DEVICE

(71) Applicant: Sanofi-Aventis Deutschland GMBH, Frankfurt am Main (DE)

(72) Inventors: Peter Nober, Rommersheim (DE); Matthias Rau, Wiesbaden (DE); David Theysen, Mainz (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 264 days.

(21) Appl. No.: 16/466,361

(22) PCT Filed: Dec. 4, 2017

(86) PCT No.: PCT/EP2017/081310
§ 371 (c)(1),
(2) Date: Jun. 4, 2019

(87) PCT Pub. No.: WO2018/104204
PCT Pub. Date: Jun. 14, 2018

(65) Prior Publication Data
US 2020/0078530 A1    Mar. 12, 2020

(30) Foreign Application Priority Data
Dec. 7, 2016   (EP) .................................. 16202660

(51) Int. Cl.
*A61M 5/32*       (2006.01)

(52) U.S. Cl.
CPC ................................ *A61M 5/3204* (2013.01)

(58) Field of Classification Search
CPC .......... A61M 5/2466; A61M 2005/247; A61M 2005/2474; A61M 5/3204; A61J 1/2096; A61J 1/2013; A61J 1/2075
See application file for complete search history.

(56) References Cited

U.S. PATENT DOCUMENTS

| 3,865,236 A | 2/1975 | Rycroft |
| 5,209,739 A | 5/1993 | Talalay |
| 2013/0218089 A1* | 8/2013 | Davies .............. A61M 5/31596 604/191 |

FOREIGN PATENT DOCUMENTS

| CN | 102481405 | 5/2012 |
| CN | 102802704 | 11/2012 |
| CN | 103191511 | 7/2013 |
| CN | 105744978 | 7/2016 |

(Continued)

OTHER PUBLICATIONS

PCT International Preliminary Report on Patentability in International Appln. No. PCT/EP2017/081310, dated Jun. 11, 2019, 9 pages.

(Continued)

*Primary Examiner* — Emily L Schmidt
(74) *Attorney, Agent, or Firm* — Fish & Richardson P.C.

(57) ABSTRACT

The present disclosure relates to cap for an injection device. The cap includes a needle shield and a conduit. The needle shield includes a body with a recess for receiving part of a needle syringe. The conduit is movable from an initial position, wherein a portion of the body is located between the recess and the conduit, to a cap removal position, wherein the conduit extends through said portion of the body to fluidly communicate with the recess to allow the ingress of gas into the recess.

16 Claims, 8 Drawing Sheets

(56) References Cited

FOREIGN PATENT DOCUMENTS

| | | |
|---|---|---|
| CN | 105848698 | 8/2016 |
| EP | 1253958 | 11/2004 |
| EP | 2440270 | 4/2012 |
| JP | 2013-542794 | 11/2013 |
| JP | 2017-538549 | 12/2017 |
| WO | WO 2001/030419 | 5/2001 |
| WO | WO 01/054758 | 8/2001 |
| WO | WO 2005/079889 | 9/2005 |
| WO | WO 2008/075033 | 6/2008 |
| WO | WO 2009/002474 | 12/2008 |
| WO | WO 2010/142813 | 12/2010 |
| WO | WO 2011/032883 | 3/2011 |
| WO | WO 2013/183464 | 12/2013 |
| WO | WO 2015/078868 | 6/2015 |
| WO | WO 2015/079219 | 6/2015 |
| WO | WO 2016/060908 | 4/2016 |
| WO | WO 2016/102299 | 6/2016 |

OTHER PUBLICATIONS

PCT International Search Report and Written Opinion in International Appln. No. PCT/EP2017/081310, dated Feb. 26, 2018, 12 pages.

\* cited by examiner

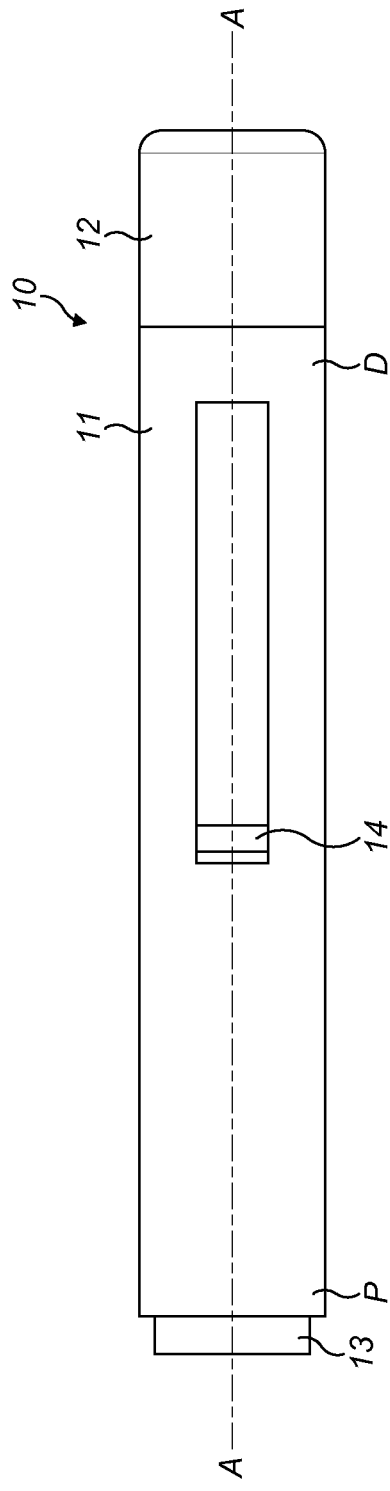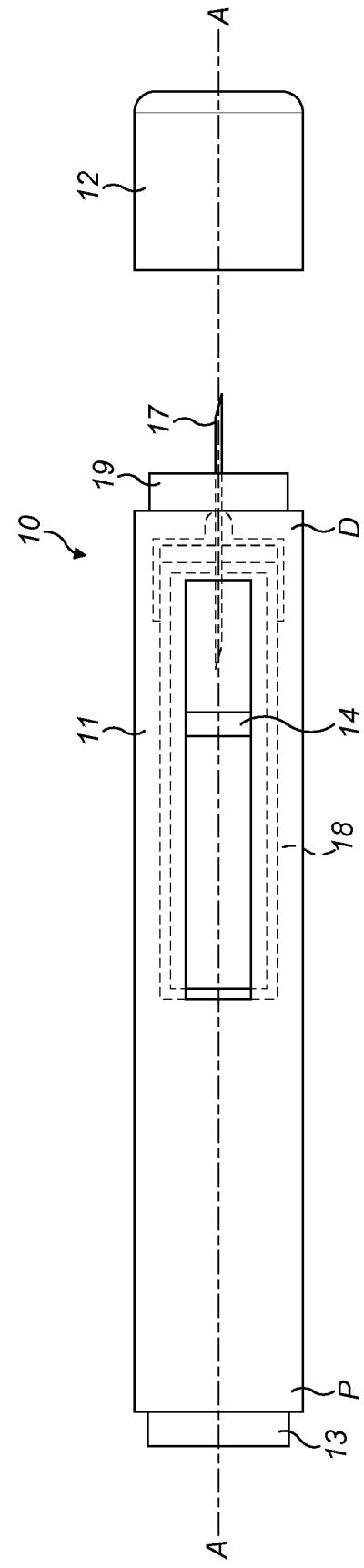
FIG. 1A
FIG. 1B

CAP FOR AN INJECTION DEVICE

CROSS REFERENCE TO RELATED APPLICATIONS

The present application is the national stage entry of International Patent Application No. PCT/EP2017/081310, filed on Dec. 4, 2017, and claims priority to Application No. EP 16202660.3 filed on Dec. 7, 2016, the disclosures of which are hereby incorporated by reference.

TECHNICAL FIELD

The present disclosure relates to a cap for an injection device and to an injection device including the same.

BACKGROUND

Injection devices, such as auto-injectors, are known in the art for dispensing a medicament to the injection site of a patient. Such injection devices typically include a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It is important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

It is an object of the present disclosure to provide an improved injection device.

According to the present disclosure, there is provided a cap for an injection device, the cap including: a needle shield including a body with a recess for receiving part of a needle syringe; and, a conduit movable from an initial position, wherein a portion of the body is located between the recess and the conduit, to a cap removal position, wherein the conduit extends through said portion of the body to fluidly communicate with the recess to allow the ingress of gas into the recess.

When the cap is removed, the body of the needle shield moves away from the needle syringe such that pressure in the recess decreases resulting in a suction effect. This suction effect results in air being drawn through the conduit and into the recess to equalise the pressure in the recess. If the cap did not include a conduit to allow for the ingress of gas into the recess during removal of the cap then the suction effect would make it more difficult for the patient to remove the needle shield from the needle syringe because the patient would need to exert a larger force on the cap to overcome the suction effect. Therefore, the conduit reduces the force that must be exerted on the cap by the patient to remove the needle shield. This is particularly advantageous if the patient is elderly or infirm. The conduit may be slidable relative to the body between the initial positon and cap removal position.

In one embodiment, the conduit includes a piercing member configured to puncture the body of the needle shield when the conduit is moved to the cap removal position. The piercing member provides a relatively simple mechanism for fluidly communicating with the recess and allows for the recess to be initially sealed until the body is punctured by the piercing member.

In one embodiment, the cap further includes an actuator that is moveable relative to the body of the needle shield to move the conduit from the initial position to the cap removal position. In one such embodiment, the actuator is located at a distal end of the cap and is slidable towards a proximal end of the cap to move the conduit to the cap removal position. Therefore, the patient may press the actuator against a flat surface, such as a table surface, and apply a force to the cap to actuate the actuator, This pressing motion simplifies operation of the cap, particularly if the patient is elderly or infirm. The conduit may be fixed relative to the actuator.

The cap may further include an outer cap, wherein the actuator is moveable relative to the outer cap to move the conduit to the cap removal position.

In one embodiment, the conduit is configured to fluidly communicate the recess with atmosphere when the conduit is in the cap removal position. Therefore, the recess equalises with atmospheric pressure once the conduit is in the cap removal position to facilitate removal of the cap.

In one embodiment, the cap further includes a compression volume, wherein the conduit is configured to fluidly communicate the compression volume with the recess when the conduit is in the cap removal position, the compression volume being compressible to increase the gas pressure in the recess. The conduit therefore equalises the pressure in the compression volume with the pressure in the recess to reduce the suction effect and thus facilitate removal of the cap. In one such embodiment, movement of the actuator relative to the body urges the piston to slide within the chamber to compress the compression volume. The compression volume may be disposed within a part of the cap, for instance, the outer cap. The compression volume may be disposed within the actuator, thereby reducing the size of the cap.

In one embodiment, the cap further includes a chamber and a piston, wherein the chamber includes the compression volume and wherein the piston is slidable within the chamber to compress the compression volume. The conduit may be fixed relative to the piston.

In one embodiment, the chamber is located within the actuator.

In one embodiment, the piston is movable relative to the actuator to compress the compression volume.

The conduit may include a sharp tip. The conduit may be substantially rigid.

In one embodiment, the cap is a cap for a medical injection device.

In one embodiment, the needle shield is configured to seal against said needle syringe and, preferably, wherein said needle syringe includes a needle hub and the body is configured to engage with the needle hub to seal the recess.

In one embodiment, the actuator is moveable from a first position to a second position to move the conduit from the initial position to the cap removal position. In one such embodiment, the cap further includes a locking mechanism configured to retain conduit in the initial position and/or retain the actuator in the second position. The locking mechanism may include first and second locking elements which engage when the actuator is in the second position.

In one embodiment, the recess is hermetically sealed when a needle syringe is received in the recess and the conduit is in the initial position.

In one embodiment, the cap further includes a removal member configured such that when the cap is removed from the needle syringe the removal member exerts a force on the needle shield to remove the needle shield. The removal member may be in the form of a flange. The flange may extend radially inwardly. In an alternative embodiment, the removal member is omitted. In one such embodiment, the cap is removed from the needle syringe and then the needle shield is subsequently removed by the patient.

The conduit may move axially between the initial position and the cap removal position. The conduit may move towards the proximal end of the injection device when moving from the initial position to the cap removal position.

The injection device may be a medical injection device.

The recess of the body of the needle shield may be configured to receive at least part of a needle hub of said needle syringe.

In one embodiment, there is provided a cap for a medical injection device, the cap including: a needle shield including a body with a recess for receiving at least part of a needle hub of a needle syringe; and, a piercing member movable from an initial position, wherein a portion of the body is located between the recess and the piercing member, to a cap removal position, wherein the piercing member punctures the body of the needle shield to fluidly communicate with the recess to allow the ingress of gas into the recess.

According to the present disclosure, there is also provided an injection device including: a needle syringe; and, a cap as described above, wherein the recess of the needle shield receives part of the needle syringe such that when the conduit is in the initial position the recess is sealed. In one embodiment, the needle syringe contains a medicament. The injection device may include an auto-injector.

According to the present disclosure, there is also provided a method of removing a cap of an injection device, wherein the injection device includes a needle syringe containing a medicament and wherein the cap includes a conduit and a needle shield, the needle shield having a recess which receives part of the needle syringe, the method including: moving the conduit from an initial position, wherein a portion of the body is located between the recess and the conduit and the recess is sealed, to a cap removal position, wherein the conduit extends through said portion of the body to fluidly communicate with the recess to allow the ingress of gas into the recess.

The injection device may include a medical injection device. The recess may receive at least part of a needle hub of the needle syringe.

The conduit may include a piercing member. The method may include moving the piercing member from an initial position, wherein a portion of the body is located between the recess and the piercing member and the recess is sealed, to a cap removal position, wherein the piercing member punctures the body of the needle shield to fluidly communicate with the recess to allow the ingress of gas into the recess.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which:

FIG. 1A is a schematic side view of an auto-injector that embodies the disclosure, with a cap attached to a body of the injection device;

FIG. 1B is a schematic side view of the auto-injector of FIG. 1A, with the cap removed from the body;

DETAILED DESCRIPTION

Figure 2:
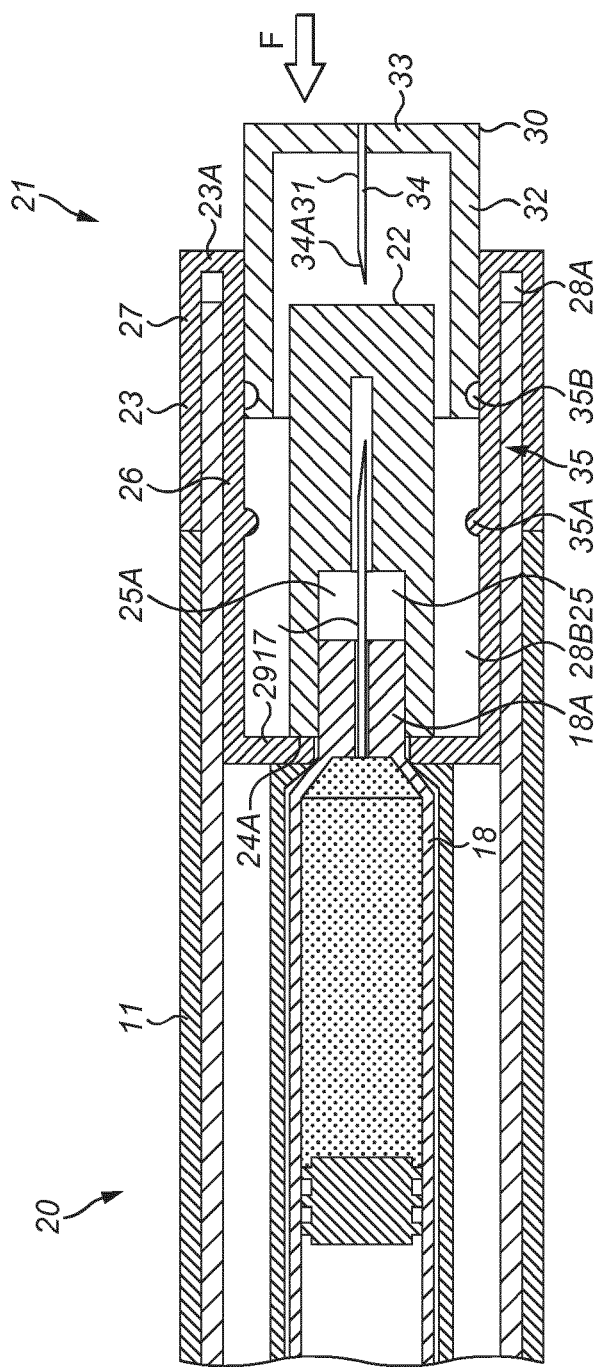
FIG. 2 is a schematic cross-sectional side view of part of an auto-injector according to a first embodiment of the disclosure, wherein a cap is attached to a body of the auto-injector and an actuator is in a first position.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 3:
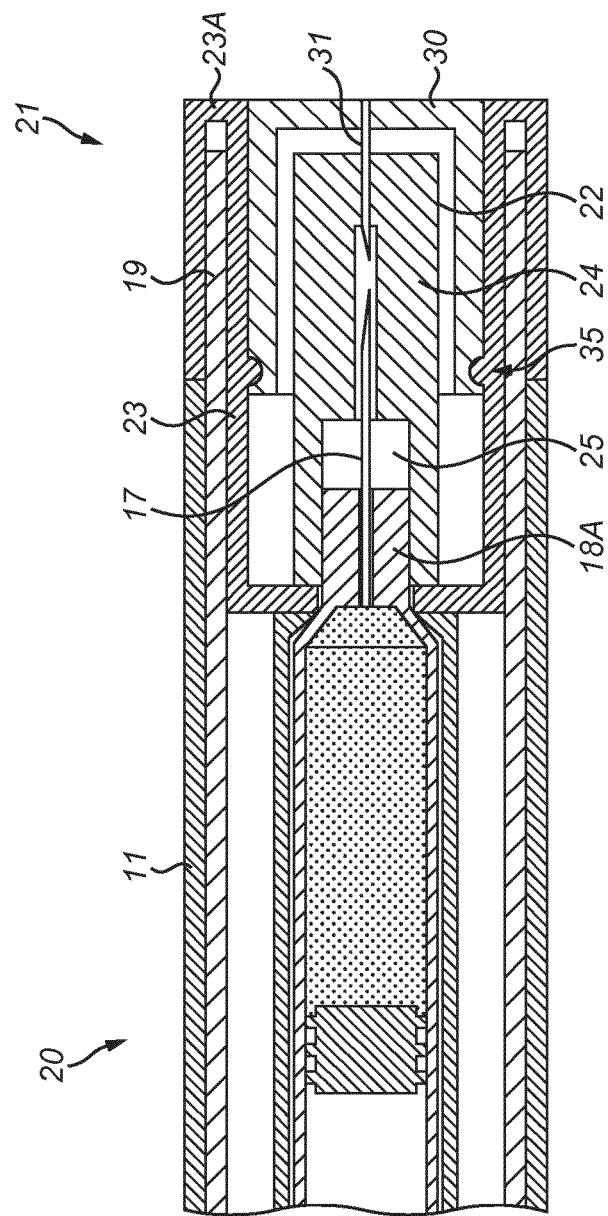
FIG. 3 is a schematic cross-sectional side view of part of the auto-injector of FIG. 2, wherein a cap is attached to a body of the auto-injector and an actuator is in a second position.
Figure 4:
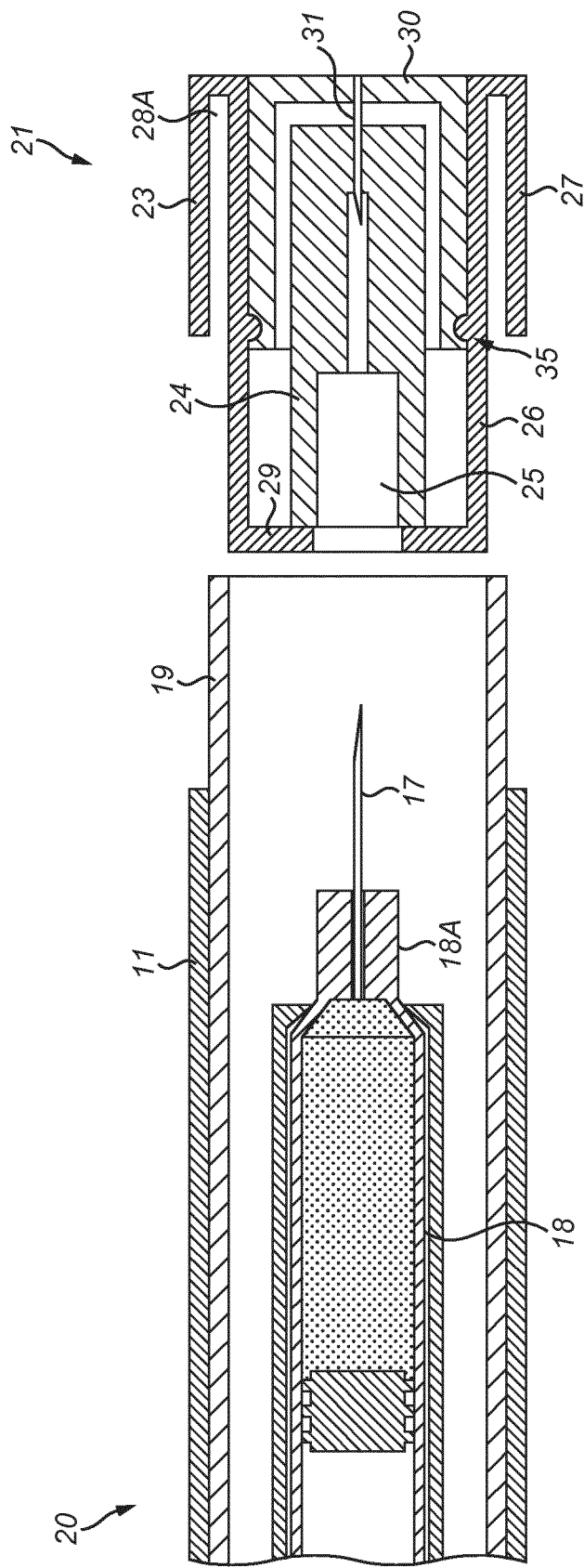
FIG. 4 is a schematic cross-sectional side view of part of the auto-injector of FIG. 2, wherein the cap is removed from the body and the actuator is in the second position.

Referring now to FIGS. 2 to 4, part of an injection device 20 according to a first embodiment of the disclosure is shown. The injection device 20 is in the form of an auto-injector 20 that has similar features to the auto-injector 10 described above in relation to FIGS. 1A and 1B, with like features retaining the same reference numerals. The auto-injector 20 of the first embodiment has a housing 11 that holds a needle syringe including a needle 17 and a syringe 18. The syringe 18 includes a needle hub 18A that is attached to the needle 17.

A difference between the auto-injector 10 described above in relation to FIGS. 1A and 1B and the auto-injector 20 of the first embodiment is that the cap 12 is omitted and is replaced with an alternative cap 21.

The cap 21 of the auto-injector 20 of the first embodiment of the disclosure includes a needle shield 22 and an outer cap 23. The needle shield 22 includes a body 24 of impermeable material with a recess 25 in a proximal end of the body 24.

The recess 25 is configured to receive the needle hub 18A and the needle 17 such that the needle 17 is shielded by the body 24. The inside surface of the body 24 and the outside surface of the needle hub 18A frictionally engage to seal the recess 25 to prevent the ingress of air into the recess 25. Thus, the needle 17 is kept sterile when the cap 21 is attached to the housing 11.

The outer cap 23 includes an inner portion 26 and an outer portion 27. The inner and outer portions 26, 27 are generally cylindrical. The inner portion 26 has a smaller diameter than the outer portion 27 and is located within the outer portion 27. The inner and outer portions 26, 27 are concentrically arranged. The inner and outer portions 26, 27 are fixedly connected to each other by an end wall 23A of the outer cap 23 located at the distal end of the auto-injector 20.

A generally annular first space 28A is located between the inner and outer portions 26, 27 of the end cap 23. The first space 28A extends to the end wall 23A of the outer cap 23. The first space 28A is shaped to correspond to the shape of the distal end of the needle sleeve 19. When the cap 21 is initially attached to the housing 11 to seal the needle 17 the needle sleeve 19 is received in the first space 28A.

The outer cap 23 further includes a removal member 29 configured such that when the outer cap 23 is removed from the housing 21 the removal member 29 exerts a force on the needle shield 22 to remove the needle shield 22 and thus expose the needle 17. The removal member 29 is in the form of a flange 29 that extends radially inwardly from a proximal end of the inner portion 26 of the outer cap 23. When the cap 21 is initially attached to the housing 11 of the auto-injector 20 the flange 29 abuts a proximal surface 24A of the body 24.

The auto-injector 20 further includes an actuator 30 and a conduit 31. The actuator 30 includes a generally cylindrical peripheral wall 32 and a generally planar end wall 33 extending from the distal end of the peripheral wall 32. The actuator 30 is generally cup-shaped.

The peripheral wall 32 of the actuator 30 is concentrically aligned with the inner and outer portions 26, 27 of the outer cap 23. The actuator 30 is slidably received within a second space 28B within the inner portion 26 of the outer cap 23.

The conduit 31 includes a piercing member 31. In the present embodiment, the piercing member 31 is in the form of a second needle 31.

The piercing member 31 includes a tube 34 with a sharp tip 34A at the proximal end of the tube 34. The distal end of the tube 34 is attached to the end wall 33 of the actuator 30 and extends through the end wall 33 such that an opening in the distal end of the tube 34 is fluidly communicated with atmosphere. Movement of the actuator 30 within the second space 28B causes corresponding movement of the piercing member 31 attached to the actuator 30.

The actuator 30 is slidable relative to the outer cap 23 from an initial position (shown in FIG. 2), wherein part of the actuator 30 protrudes distally from the outer cap 23, to a second position (shown in FIGS. 3 and 4), wherein the actuator 30 is slid proximally such that the actuator 30 moves into the inner portion 26 of the outer cap 23 until the end wall 33 of the actuator 30 is flush with the end wall 23A of the outer cap 23.

When the actuator 30 is in the first position, the piercing member 31 is in an initial position wherein the tube 34 extends proximally from the end wall 33 of the actuator 30 towards the body 24 of the needle shield 22. The tip 34A is spaced from the body 24 such that a portion of the body 24 is located between the tip 34A and the recess 25 and thus the recess 25 is sealed from the conduit 31. When the actuator 30 is moved to the second position, the piercing member 31 moves to a cap removal position wherein the tip 34A pierces the body 24 such that the piercing member 31 penetrates said portion of the body 24 and extends into the recess 25. Therefore, when the piercing member 31 is in the cap removal position, atmospheric air is able to flow through the tube 34 of the piercing member 31 and into the recess 25 of the needle shield 22.

A locking mechanism 35 is provided to retain the actuator 30 in the second position. The locking mechanism 35 includes pairs of first and second locking elements 35A, 35B which engage when the actuator 30 is in the second position. The pair of first locking elements 35A includes a pair of protrusions 35A that each extend radially inwardly from the inner portion 26 of the outer cap 23. The pair of second locking elements 35B includes a pair of recesses 35B that are each formed in the outer surface of the body 24 of the needle shield 22.

When the actuator 30 is moved from the first position to the second position, each protrusion 35A snaps into a respective recess 35B of the locking mechanism 35 to retain the actuator 30 in the second position.

In an alternative embodiment (not shown), the first locking elements each include a recess formed in the inner portion of the outer cap and the second locking elements each include a protrusion that extends radially outwardly from the body of the needle shield to be received in a respective recess. In another embodiment (not shown), the locking element includes a single first locking element and a single second locking element. In one embodiment, the first locking element includes an annular groove and the second locking element includes an annular ridge that is received in the annular groove when the actuator is in the second position.

The cap 21 is initially attached to the housing 11 such that the needle 17 and the needle hub 18A are received in the recess 25 of the needle shield 22. Thus, the needle 17 is covered by the needle shield 22 and hermetically sealed to keep the needle 17 sterile and to prevent the needle 17 from causing injury to the patient. When the cap 21 is initially attached to the housing 11, the needle sleeve 19 is received in the first recess 28A of the outer cap 23, the actuator 30 is in the first position (as shown in FIG. 2), and the piercing member 31 is in the initial position.

To inject medicament, the cap 21 is first removed from the housing 11 of the auto-injector 20 to expose the needle 17. Removal of the cap 21 from the housing 11 is achieved by the patient exerting a force on the actuator 30 (in the direction of arrow 'F' in FIG. 2) to urge the actuator 30 proximally towards the housing 11. This causes the actuator 30 to slide relative to the outer cap 23 from the first position (as shown in FIG. 2) to the second position (as shown in FIG. 3) such that the piercing member 31 is urged from the initial positon to the cap removal position, wherein the piercing member 31 penetrates the body 24 of the needle shield 22 such that the recess 25 is fluidly communicated with atmosphere. The actuator 30 is retained in the second position by the locking mechanism 35.

The patient then grips the outer cap 23 and pulls the outer cap 23 distally away from the housing 11 to remove the outer cap 23. This causes the flange 29 to be urged against the proximal surface 24A of the body 24 of the needle shield 22 such that the needle shield 22 is removed from the needle 17 (as shown in FIG. 4).

With the cap 21 removed from the housing 11, the needle sleeve 19 protrudes from the distal end of the housing 11 to shield the needle 17. The distal end of the needle sleeve 19 is then pressed against an injection site of the patient such that the needle sleeve 19 retracts into the housing 11 and the needle 17 enters the injection site. The dispense button (not shown) is then pressed to dispense medicament to the injection site.

When the cap 21 is initially attached to the housing 11 and the actuator 30 is in the first position, a space 25A is disposed in the recess 25 between the body 24 of the needle shield 22 and the needle hub 18A. The space 25A contains a gas, for example, air or carbon dioxide, which enters the recess 25 during assembly of the auto-injector 20. When the cap 21 is removed, the body 24 of the needle shield 22 moves distally away from the needle hub 18A and therefore the volume of the space 25A increases. This causes a suction effect which results in air being drawn through the piercing member 31 and into the space 25A to equalise the pressure in the space 25A with atmospheric pressure. If the auto-injector 20 did not include a conduit 31 to allow for the ingress of gas into the recess 25 during removal of the cap 21 then the suction effect would make it difficult for the patient to remove the needle shield 22 from the needle hub 18A because the patient would need to exert a large force on the cap 21 to overcome the suction effect. Therefore, the conduit 31 reduces the force that must be exerted on the cap 21 by the patient to remove the needle shield 22. This is particularly advantageous if the patient is elderly or infirm.

Referring now to FIGS. 5 to 8, part of an injection device 40 according to a second embodiment of the disclosure is shown. The injection device 40 is in the form of an auto-injector 40 that has similar features to the auto-injector 20 described above in relation to FIGS. 2 to 4, with like features retaining the same reference numerals. A difference is that the cap 21 of the auto-injector 20 described above is omitted and is replaced with an alternative cap 41.

The cap 41 of the auto-injector 40 of the second embodiment includes a needle shield 22 and an outer cap 23. The needle shield 22 includes a body 24 of impermeable material with a recess 25 in the proximal end of the body 24. The recess 25 is configured to receive the needle hub 18A and the needle 17 such that the needle 17 is shielded by the body 24. The inside surface of the body 24 and the outside surface of the needle hub 18A frictionally engage to seal the recess 25 to prevent the ingress of air into the recess 25. Thus, the needle 17 is kept sterile when the cap 41 is attached to the housing 11.

As with the first embodiment, the outer cap 23 includes an inner portion 26 and an outer portion 27 located radially outwardly of the inner portion 26. The inner and outer portions 26, 27 are fixedly connected to each other by an end wall 23A of the outer cap 23 located at the distal end of the outer cap 23. When the cap 41 is initially attached to the housing 11 the needle sleeve 19 is received in a first space 28A between the inner and outer portions 26, 27.

The outer cap 23 further includes a removal member 29 configured such that when the outer cap 23 is removed from the housing 11 the removal member 29 exerts a force on the needle shield 22 to remove the needle shield 22. The removal member 29 includes a flange 29 that abuts a proximal surface 24A of the body 24 when the cap 41 is attached to the housing 11.

The auto-injector 40 further includes an actuator 50 and a conduit 51. The actuator 50 includes a generally cylindrical peripheral wall 52 and a generally planar end wall 53 extending from the distal end of the peripheral wall 52. The actuator 50 is generally cup-shaped.

The peripheral wall 52 of the actuator 50 is concentrically aligned with the inner and outer portions 26, 27 of the outer cap 23. The actuator 50 is slidably received within a second space 28B within the inner portion 26 of the outer cap 23.

The conduit 51 includes a piercing member 51. In the present embodiment, the piercing member 51 is in the form of a second needle 51.

The piercing member 51 includes a tube 54 with a sharp tip 54A at the proximal end of the tube 54.

The auto-injector 40 further includes a piston 56. The peripheral wall 52 and end wall 53 of the actuator 50 define a chamber 57 and the piston 56 is slidably received in the chamber 57 such that a compression volume 58 is formed in the chamber 57 between the piston 56 and the end wall 53.

The piercing member 51 is attached to the piston 56 and extends proximally. The tube 54 extends through the piston 56 such that an opening in the distal end of the tube 54 is fluidly communicated with the compression volume 58.

Figure 5:
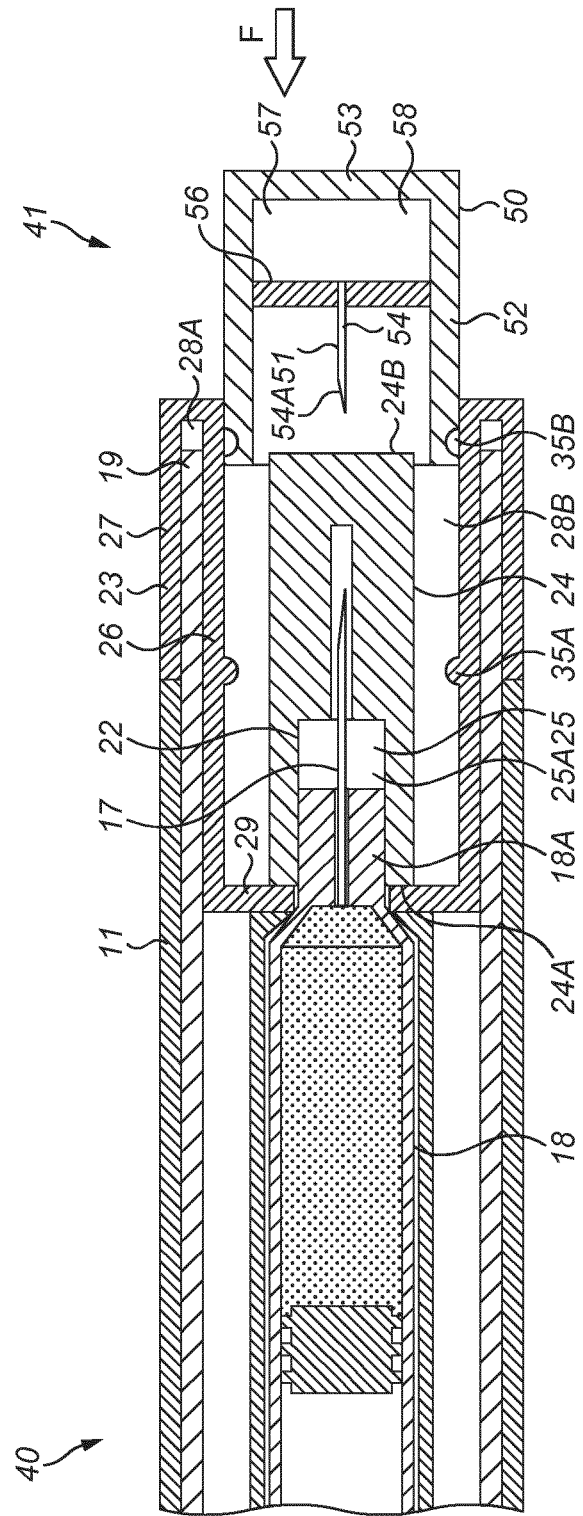
FIG. 5 is a schematic cross-sectional side view of part of an auto-injector according to a second embodiment of the disclosure, wherein a cap is attached to a body of the auto-injector and an actuator is in a first position.

The actuator 50 is slidable relative to the outer cap 23 from an initial position (as shown in FIG. 5), wherein part of the actuator 50 protrudes distally from the outer cap 23, to an intermediate position (shown in FIG. 6), wherein the actuator 50 is slid proximally into the outer cap 23 to be partially received in the second space 28B of the outer cap 23. From the intermediate position the actuator 50 is moveable to a second position (shown in FIGS. 7 and 8), wherein the actuator 50 is slid proximally such that the actuator 50 moves into the inner portion 26 of the outer cap 23 until the end wall 53 of the actuator 50 is flush with the end wall 23A of the outer cap 23.

Figure 6:
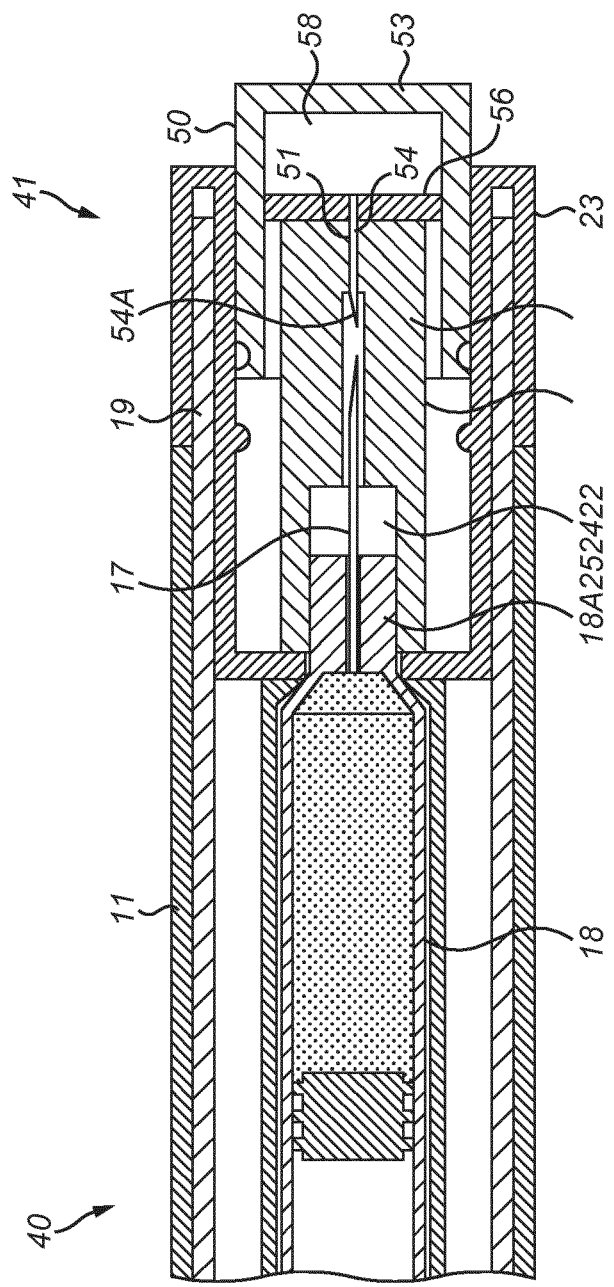
FIG. 6 is a schematic cross-sectional side view of part of the auto-injector of FIG. 5, wherein the cap is attached to the body and the actuator is in an intermediate position.

When the actuator 50 is in the first position, the piercing member 51 is in an initial position wherein the tube 54 extends proximally from the piston 56 towards the body 24 of the needle shield 22. The tip 54A is spaced from the body 24 such that a portion of the body 24 is located between the tip 54A and the recess 25 and thus the recess 25 is sealed from the piercing member 51. When the actuator 50 is moved to the intermediate position, the piercing member 51 moves to a cap removal position wherein the tip 54A pierces the body 24 such that the piercing member 51 penetrates said portion of the body 24 and extends into the recess 25 (as shown in FIG. 6). Therefore, when the piercing member 51 is in the cap removal position, gas in the compression volume 58 is able to flow through the tube 54 of the piercing member 51 and into the recess 25 of the needle shield 22 to equalise the pressure in the recess 25 with the pressure in the compression volume 58. Thus, compression of the gas in the compression volume 58 will increase the pressure in the recess 25, as will be explained below.

The cap 41 is initially attached to the housing 11 such that the needle 17 and the needle hub 18A are received in the recess 25 of the needle shield 22. Thus, the needle 17 is covered by the needle shield 22 and hermetically sealed to keep the needle 17 sterile and to prevent the needle 17 from causing injury to the patient. When the cap 41 is initially attached to the housing 11, the needle sleeve 19 is received in the first recess 28A of the outer cap 23, the actuator 50 is in the first position (as shown in FIG. 5), and the piercing member 51 is in the initial position.

To inject medicament, the cap 41 is first removed from the housing 11 of the auto-injector 40 to expose the needle 17. Removal of the cap 41 from the housing 11 is achieved by the patient first exerting a force on the actuator 50 (in the direction of arrow 'F' in FIG. 5) to urge the actuator 50 proximally towards the housing 11. This causes the actuator 50 to slide relative to the outer cap 23 from the first position (as shown in FIG. 5) to the intermediate position (as shown in FIG. 6) such that the piercing member 51 is urged from the initial positon to the cap removal position, wherein the piercing member 51 penetrates the body 24 of the needle shield 22 such that the recess 25 is fluidly communicated with the compression volume 58. When the piercing member 51 is in the cap removal position, the piston 56 abuts a distal surface 24B of the body 24 of the needle shield 22.

Figure 7:
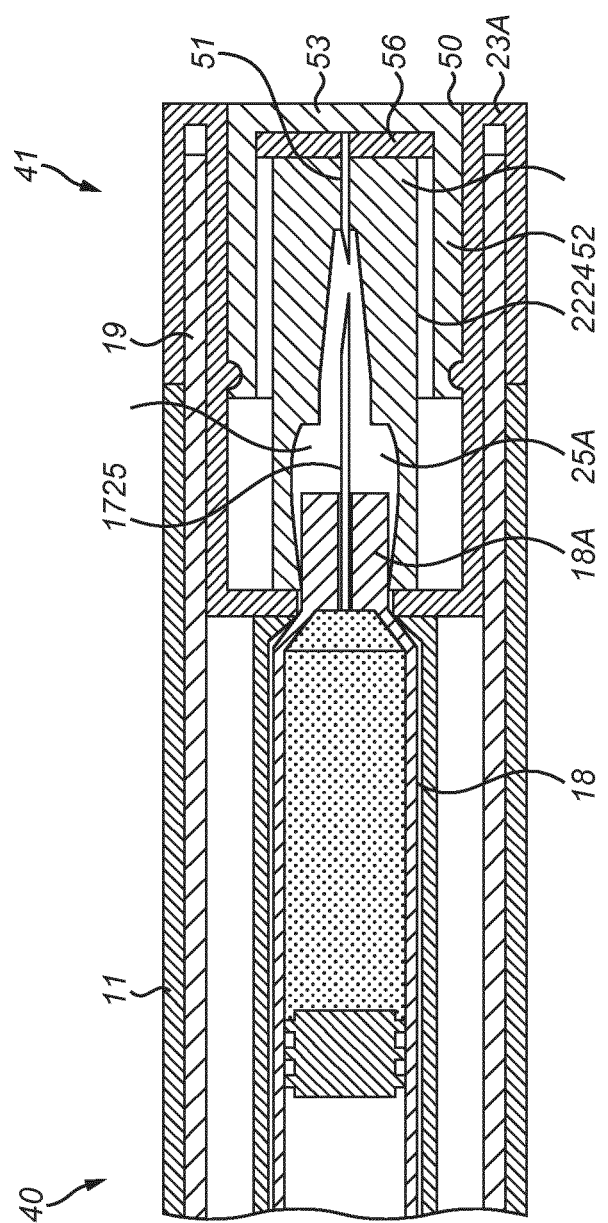
FIG. 7 is a schematic cross-sectional side view of part of the auto-injector of FIG. 5, wherein the cap is attached to the body and the actuator is in a second position; and, FIG. 8 is a schematic cross-sectional side view of part of the auto-injector of FIG. 5, wherein the cap is removed from the body and the actuator is in the second position.

The patient continues to exert a force on the actuator 50 (in the direction of arrow 'F') to urge the actuator 50 towards the housing 11 such that the actuator 50 is moved to the second position (as shown in FIG. 7). This causes the end wall 53 of the actuator 50 to move towards the piston 56 such that the compression volume 58 is compressed and thus the pressure of gas, for example, air or carbon dioxide, in the compression volume 58 is increased. The piercing member 51 equalises the pressure in the compression volume 58 with the pressure in the recess 25 and therefore movement of the actuator 50 from the intermediate position to the second position increases the pressure of the gas in the recess 25. The actuator 50 is retained in the second position by the locking mechanism 35.

The pressure in the compression volume 58 and in the recess 25 is above atmospheric pressure when the actuator 50 is in the second position. Thus, the gas in the recess 25 acts on the needle hub 18A and the body 24 to exert a force on the needle shield 22 to urge the needle shield 22 distally away from the housing 11.

Figure 8:
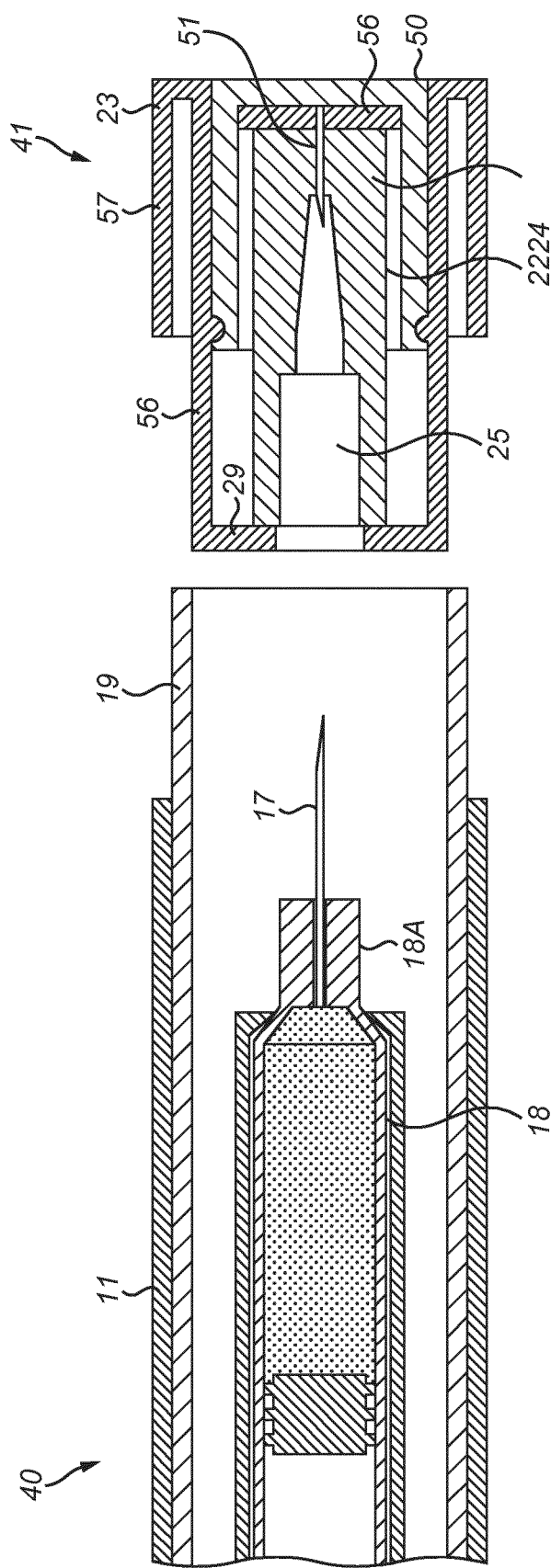

The patient then grips the outer cap 23 and pulls the outer cap 23 distally away from the housing 11 to remove the outer cap 23. This causes the flange 29 to be urged against the needle shield 22 such that the needle shield 22 is removed from the needle 17 (as shown in FIG. 8). With the cap 41 removed from the housing 11, the needle sleeve 19 protrudes from the distal end of the housing 11 to shield the needle 17. The distal end of the needle sleeve 19 is then pressed against an injection site of the patient such that the needle sleeve 19 retracts into the housing 11 and the needle 17 enters the injection site. The dispense button (not shown) is then pressed to dispense medicament to the injection site.

In the present embodiment, the force exerted on the needle shield 22 by the gas in the recess 25 when the actuator 50 is in the second position is insufficient to move the needle shield 22 away from the housing 11. In other words, said force is not large enough to overcome the friction between the needle hub 18A and the body 24 of the needle shield 22. However, the force exerted on the needle shield 22 by the gas in the recess 25 when the actuator 50 is in the second position reduces the size of the force that must be exerted on the outer cap 23 by the patient to remove the needle shield 22 and thus makes removal of the cap 41 easier.

In an alternative embodiment (not shown), the force exerted on the needle shield 22 by the gas in the recess 25 when the actuator 50 is in the second position is large enough to overcome the friction between the needle hub 18A and the body 24 of the needle shield 22. Therefore, upon movement of the actuator 50 to the second position, the needle shield 22 is urged away from the housing 11 due to the force exerted on the needle shield 22 by the gas pressure in the recess 25 such that the needle shield 22 is removed from the needle hub 18A. Once the needle hub 18A has been fully removed from the recess 25, the friction between the cap 41 and the housing 11 and/or needle sleeve 19 is minimal such that the cap 41 can easily be removed from the housing 11 simply by pulling the cap 41 away from the housing 11 to expose the needle 17.

In the above described embodiments, the actuator 30, 50 is slidable relative to the outer cap 23 to move the conduit 31, 51 from the initial position to the cap removal position. However, in an alternative embodiment (not shown), the actuator is fixed relative to the outer cap and both the actuator and outer cap are moveable together relative to the needle shield to move the conduit from the initial position to the cap removal position.

In some embodiments (not shown), the outer cap 23 is omitted. In one such embodiment, the actuator is slidably mounted to the needle shield and the conduit is attached to the actuator. The actuator is slid relative to the needle shield to urge the conduit from the initial position to the cap removal position.

In the above described embodiments, the conduit 31, 51 moves relative to the needle shield 22 in the direction of the longitudinal axis A-A of the auto-injector 20, 40 from the initial position to the cap removal position. However, it should be recognised that the conduit 31, 51 may instead be configured to move in a different direction relative to the needle shield 22, for example, at an angle to the longitudinal axis A-A from the initial position to the cap removal position. In one embodiment (not shown), the conduit 31, 51 moves radially with respect to the needle shield 22 from the initial position to the cap removal position.

In the above embodiments, when the needle hub 18A is received in the recess 25 and the conduit 31, 51 is in the initial position, the recess 25 is hermetically sealed such that the ingress of air or gas into the recess 25 is prevented. However, in an alternative embodiment (not shown), the recess is not completely airtight or gastight.

In the above described embodiments, the outer cap 23 includes a removal member 29 that is configured to remove the needle shield 22 when the patient removes the outer cap 23. However, it should be recognised that in alternative embodiments (not shown) the removal member is omitted. In one such embodiment (not shown), the patient first removes the outer cap and then separately removes the needle shield.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-630) human insulin; Des (B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(ω-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A cap for an injection device, the cap comprising:
a needle shield comprising a body with a recess for receiving part of a needle syringe;
and a conduit movable from an initial position wherein a portion of the body is located between the recess and the conduit, to a cap removal position wherein the conduit extends through the portion of the body to fluidly communicate with the recess to allow an ingress of gas into the recess,
wherein the ingress of the gas into the recess via the conduit reduces a force that must be exerted on the cap to remove the needle shield from the injection device.

2. A cap according to claim 1, wherein the conduit comprises a piercing member configured to puncture the body of the needle shield when the conduit is moved to the cap removal position.

3. A cap according to claim 1, further comprising an actuator that is moveable relative to the body of the needle shield to move the conduit from the initial position to the cap removal position.

4. A cap according to claim 3, wherein the actuator is located at a distal end of the cap and is slidable towards a proximal end of the cap to move the conduit to the cap removal position.

5. A cap according to claim 3, further comprising an outer cap, wherein the actuator is moveable relative to the outer cap to move the conduit to the cap removal position.

6. A cap according to claim 3, wherein the conduit is fixed relative to the actuator.

7. A cap according to claim 3, further comprising a compression volume, wherein the conduit is configured to fluidly communicate the compression volume with the recess when the conduit is in the cap removal position, the compression volume being compressible to increase the gas pressure in the recess.

8. A cap according to claim 7, further comprising a chamber and a piston, wherein the chamber comprises the compression volume and wherein the piston is slidable within the chamber to compress the compression volume.

9. A cap according to claim 8, wherein the conduit is fixed relative to the piston.

10. A cap according to claim 8, wherein movement of the actuator relative to the body urges the piston to slide within the chamber to compress the compression volume.

11. A cap according to claim 10, wherein the compression volume is disposed within the actuator.

12. A cap according to claim 1, wherein the conduit is configured to fluidly communicate the recess with atmosphere when the conduit is in the cap removal position.

13. A cap according to claim 1, wherein the needle shield is configured to seal against the needle syringe and, wherein the needle syringe comprises a needle hub and the body is configured to engage with the needle hub to seal the recess.

14. An injection device comprising:
a needle syringe; and
a cap, comprising:
a needle shield comprising a body with a recess for receiving part of the needle syringe, and
a conduit movable from an initial position wherein a portion of the body is located between the recess and the conduit, to a cap removal position wherein the conduit extends through the portion of the body to fluidly communicate with the recess to allow an ingress of gas into the recess,
wherein the recess of the needle shield receives part of the needle syringe such that when the conduit is in the initial position, the recess is sealed,
wherein the ingress of the gas into the recess via the conduit reduces a force that must be exerted on the cap to remove the needle shield from the injection device.

15. An injection device according to claim 14, wherein the needle syringe contains a medicament.

16. A method of removing a cap of an injection device, wherein the injection device comprises a needle syringe containing a medicament and wherein the cap comprises a conduit and a needle shield, the needle shield having a body with a recess which receives part of the needle syringe, the method comprising:

moving the conduit from an initial position wherein a portion of the body is located between the recess and the conduit and wherein the recess is sealed, to a cap removal position wherein the conduit extends through the portion of the body to fluidly communicate with the recess to allow an ingress of gas into the recess, wherein the ingress of the gas into the recess via the conduit reduces a force that must be exerted on the cap to remove the needle shield from the injection device.

\* \* \* \* \*